United States Patent [19]

Christenson et al.

[11] Patent Number: 4,880,775
[45] Date of Patent: Nov. 14, 1989

[54] POLY-ALKYLATED BENZODIOXIN MUSK COMPOSITIONS

[75] Inventors: Philip A. Christenson, Midland Park; Brian Drake, Clifton; Paul J. Riker, Lodi, all of N.J.

[73] Assignee: BASF K&F Corporation, Parsippany, N.J.

[21] Appl. No.: 305,373

[22] Filed: Feb. 1, 1987

[51] Int. Cl.$^4$ .............................................. A01K 7/46
[52] U.S. Cl. ...................................... 512/12; 549/365; 568/781
[58] Field of Search ......................... 549/365; 512/12; 568/781

[56] References Cited

U.S. PATENT DOCUMENTS

| | | | |
|---|---|---|---|
| 2,769,014 | 10/1956 | Gerret | 512/12 |
| 2,789,985 | 4/1957 | Harrison | 549/365 |
| 3,326,746 | 6/1967 | Cahn et al. | 512/12 |
| 3,496,193 | 2/1970 | Heywood et al. | 512/12 |
| 4,000,311 | 12/1976 | Gatyi et al. | 549/365 |
| 4,294,727 | 10/1981 | Conrad et al. | 512/12 |

OTHER PUBLICATIONS

Cookson et al, J. Chem. Soc. (1976), pp. 195–200.
Sartori et al., Chem. Ind. (1985), pp. 762–763.

Primary Examiner—James H. Reamer
Attorney, Agent, or Firm—Kenyon & Kenyon

[57] ABSTRACT

The present invention relates to novel poly-alkylated benzodioxin compounds possessing a musk-like aroma which are useful as fragrance materials. The compounds of the invention have the formula:

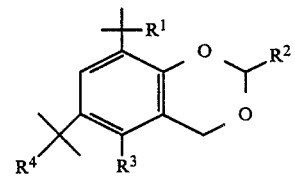

where $R^1$ to $R^4$ are hydrogen or lower alkyl ($C_1$ to $C_5$), provided that the compound has no more than 18 carbon atoms. The invention provides for synthesis of a novel phenolic intermediate and synthesis of the compounds of the invention. The invention also provides fragrance compositions which utilize the compounds of the invention to modify, enhance, or impart a musk-like aroma to perfume compositions, colognes and perfumed articles.

18 Claims, No Drawings

POLY-ALKYLATED BENZODIOXIN MUSK COMPOSITIONS

FIELD OF THE INVENTION

This invention relates to novel compounds useful as fragrances, particularly those possessing a musk-like aroma. The invention also provides a process for preparing these compounds and fragrance compositions including these compounds.

BACKGROUND OF THE INVENTION

Natural sources of musk or musk-like odor have been prized in perfumery. In the fragrance industry, however, natural materials have largely been supplanted by readily available synthetics with musk-like odors. One of the most important commercial musks, the dinitro-material 1, below, was discovered by Baur nearly 100 years ago. However, because of questions concerning the safety of the nitro-musks, there is a need in the fragrance industry for new synthetic musks which can be used as replacements for the nitro-musks, especially the dinitro-material 1.

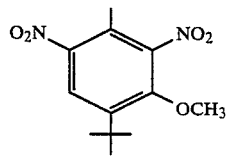

1

Many materials which possess a musk-like odor have been prepared by chemists over the years and are known to those skilled in the art. Much of the early work on synthetics is described in review articles by T. F. Wood in *Givaudanian* between 1968 and 1970. The preparation and must-like odor of napthodioxepins was reported by R. C. Cookson et al., *J. Chem. Soc.* (1976) 195–200. More recently, the chemistry of musk has been discussed in "*Fragrance Chemistry; The Science of the Sense of Smell*, edited by E. T. Thiemer (1982). In Thiemer's book, Chapter 12, an article by B. D. Mookheyee and R. A. Wilson, discusses natural musk materials and Chapters 13 and 14 by T. F. Wood discuss synthetic musk. Benzenoid must materials generally contain an electron-withdrawing substituent on the aromatic ring, such as a nitro, nitrile or carbonyl group.

Compounds 2 and 3 are the subjects of recent U.S. Pat. Nos. 4,476,040 and 4,483,786, respectively.

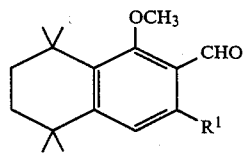

2

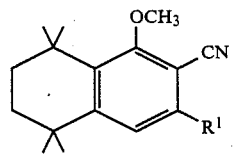

3 wherein $R^1$ is methyl or ethyl.

These known materials, however, have complex structures and/or are difficult to synthesize. In addition, questions concerning the safety of the commercially successful nitro-musks have created a need in the fragrance industry for synthetic replacements. Therefore, it is an object of the invention to prepare novel compounds that are devoid of nitro groups or other potentially hazardous functionality yet possesses a strong must note resembling in character the nitro-musk 1. Yet another object is to develop a compound that is synthetically easy to prepare.

SUMMARY OF THE INVENTION

These and other objects are achieved by the present invention which is directed to novel substituted benzodioxin compounds possessing a musk-like odor. These compounds have the formula:

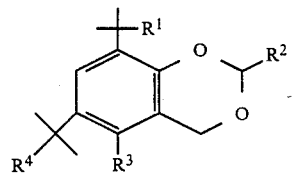

4 wherein $R^1$ to $R^4$ are hydrogen or lower alkyl ($C_1$ to $C_5$), provided that the compound has no more than 18 carbon atoms. The strength of the musk-like odor decreases where the substituted benzodioxin contains greater than 18 carbon atoms.

The present invention also provides efficient and economical processes for preparing these compounds. Thus, for example, condensation of an alkylated phenol with formaldehyde in the presence of an acid catalyst yields the benzodioxin 4 to alternatively, the alkylted phenol can be reacted with formaldehyde in the presence of base to form an intermediate diol which is further condensed with an aldehyde to form the benzodioxin 4.

It has been found that the above benzodioxins and all of their enantiomers are useful as fragrance materials. Useful fragrance compositions have been prepared by incorporating these benzodioxins individually or as admixtures.

DETAILED DESCRIPTION OF THE INVENTION

The compounds of the present invention are especially useful as substitutes for nitro-musks, described above as the dinitro-material 1. Illustrative examples of compounds falling within the scope of this invention and a description of their odors are presented below in Table I.

TABLE I

| Compound Structure | Odor Description |
| --- | --- |
| <br>5 | Strong musk, resembling in character nitro-musk 1. |

TABLE I-continued

| Compound Structure | Odor Description |
|---|---|
| 6 | Strong musk, resembling nitro-musk 1 |
| 7 | Weak musk |
| 8 | Low keyed, woody, oily musk |
| 9 | Low-keyed musk with a benzyl benzoate-like note |
| 10 | Weak, woody note with a musk nuance |

The compounds of this invention may be conveniently prepared from the corresponding phenols 11 by either of the two following schemes. Scheme I is the preferred method embodying a facile, single step, high yielding synthetic route to the benzodioxin compounds of the invention.

Scheme I

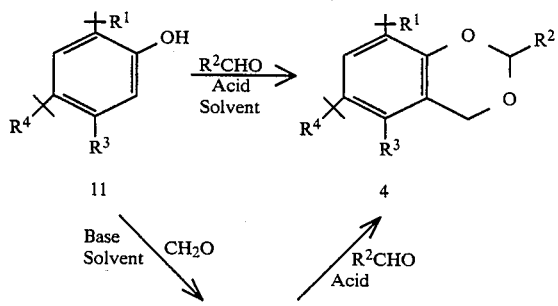

Scheme II

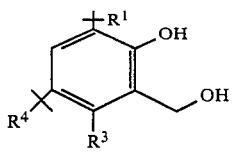

In Scheme I, condensation of phenol 11 with formaldehyde in the presence of an acid catalyst provides compound 4 ($R^2=H$). Formaldehyde may be employed in any of its forms in this reaction. Lewis acids or protic acids may be used in the reaction, the preferred acids being protic acids such as sulfuric acid, phosphoric acid, p-toluenesulfonic acid, camphorsulphonic acid, boric acid, trifluoroacetic acid, hydrochloric acid, acidic ion-exchange resins and acidic clays. The most preferred acid catalysts are sulfuric acid and p-toluenesulfonic acid.

A wide range of solvents may be used in the process of Scheme I, for example, toluene, hexane, dichloroethane, dimethoxyethane, p-dioxane, dimethylformamide, 2-methoxyethanol, tetrahydrofuran, triethylene glycol and mixtures of the above. The preferred solvents include dichloroethane, hexane, toluene, p-dioxane, dimethoxyethane, 2-methoxyethanol and tetrahydrofuran, the most preferred solvents being p-dioxane, dimethoxyethane, tetrahydrofuran and hexane. The process of Scheme I may be conducted in the temperature range of about 0° C. to 150° C., the preferred temperature range being 50° to 125° C. and the most preferred temperature range being 75° C. to 115° C.

In the process of Scheme II, the phenol 11 is condensed with formaldehyde in any of its forms in the presence of a base to provide diols 12. The diols 12 are then condensed with an aldehyde in the presence of an acid to provide comound 4. Alkali metal hydroxides, N-substituted ammonium hydroxides or alkyl amines may be used as bases in the process of Scheme II, the preferred bases being alkali metal hydroxides, the most preferred bases being sodium and potassium hydroxode.

Protic or aprotic solvents in the presence of a phase-transfer catalyst may be used as the solvent in Scheme II. The preferred solvents according to the invention include water, dimethylformamide, t-butanol, ethanol, dimethoxyethane, toluene, methoxyethanol, tetrahydrofuran and hexane, the most preferred solvents being water, dimethylformamide, tetrahydrofuran and toluene.

Phase-transfer catalysts which may be used include polyethylene glycols, tetraalkyl ammonium salts and cyclic polyethers. Polyethylene glycols are the most preferred phase-transfer catalysts. The process of Scheme II may be conducted in the temperature range of about 25° C. to 150° C., the preferred temperature range being 50° C. to 125° C. and the most preferred range being 75° C. to 125° C.

The conversions of diols 12 to the compounds 4 are achieved by employing reaction conditions similar to those used for the conversion of compound 7 to 4 ($R^2=H$) with the proviso that lower alkyl ($C_1$ to $C_5$) aldehydes may be used as well as formaldehyde.

The compounds prepared according to the invention may be isolated and purified via conventional techniques such as extraction, chromatography, distillation, crystallization and the like.

The phenol intermediates (compounds 11,) used to prepare the compounds of the invention are readily available.

The intermediate to compounds 5 and 9, 4-(1,1-dimethylethyl)-2-(1-methylethyl)-5-methylphenol, is new and can be prepared from thymol as described in Example 1. The preferred method is described in Example 1, however, isobutylene may be substituted for t-butanol.

In general, the phenol intermediates (compounds 11) may be prepared according to alkylation procedures known in the art. For example, 4-(1,1-dimethylpropyl)-2-(1-methylethyl)-5-methylphenol, the intermediate to compound 8, may be prepared as described by W. Koenigs and R. W. Carl, *Chem. Ber.*, (1981), 25, 3892–3903.

Likewise, 2,5-dimethyl-4-(1,1-dimethylethyl)-phenol, the intermediate to the compound described by Example 11, may be prepared as described by W. Weinrich, *Ind. Eng. Chem.*, (1943), 35, 264–272.

The intermediate to compounds 6 and 10, 2,4-(1,1-dimethylethyl)-phenol, is commercially available.

The compounds of the invention exhibit a range of musk aromas from strong musks resembling the nitromusk 1 to low-keyed musks with woody or benzyl benzoate-like notes. The fragrance properties attributed to the compounds of the invention were determined by submitting each to a panel of expert perfumers. The perfumery staff evaluated the fragrance properties by smelling the pure compound on a blotter when freshly blottered and at dry down, a condition occurring after several hours of evaporation. The compounds were also evaluated by mixing them with other fragrance materials and evaluating their usefulness in a finished product. The results of the evaluations are summarized in Table 1.

On the basis of their valuable olfactory properties, the inventive compounds have been found to be suitable for use in fine fragrance compositions, as well as in perfumed products, such as soaps, detergents, deodorants, cosmetic preparations and the like. Such fragrance compositions may comprise an organoleptically effective amount of one or more of the novel compounds and at least one other organoleptic agent. An "organoleptically effective amount" is a level or amount of novel compound(s) present in a perfume composition or perfumed article at which the incorporated compound(s) exhibit(s) a sensory effect.

Perfume compositions are carefully balanced, harmonious blends of essential oils, aroma chemicals, resinoids and other extracts of natural odorous materials. Each ingredient imparts its own characteristic effect to the composition. However, the overall sensory effect of the perfume composition will be at least the sum total of the effects of each of the ingredients. Substances possessing musk-like odor are known to enhance the sensor effect of nonmusk components. One or more of the novel compounds of this invention can be used to alter, modify or enhance the aroma characteristics of a perfume composition, for example, by utilizing or moderating the olfactory reaction constributed by another ingredient in the composition.

The terms "alter" and "modify" are used herein to means supply or impart an aroma character or note to otherwise relatively odorless substances, or augment the existing fragrance or aroma impression to modify its quality, character or odor. The term "enhance" is used herein to mean the amplification or intensification of the quality thereof.

The amount of the compound(s) of the invention which will be effective in perfume compositions as well as in perfume articles and colognes depends on many factors. Such factors include the other ingredients in the composition or article, their concentrations, and the overall sensory effect desired. The compound(s) can be used in amounts of as little as 0.01% and often as low as 0.0001% to impart significant odor characteristics to perfumed articles e.g. soaps, detergents, cosmetics, fabric softener compositions or articles, and other products. The amount employed can range up to about 80% of the fragrance components and up to about 7.0% of the quantity of perfumed articles and will depend on considerations of cost, nature of the end product, the effect desired on the finished product, and the particular fragrance sought.

The compound(s) of the invention may be used alone or in combination with other ingredients in perfume compositions or as (an) olfactory component(s) in lacquers, brilliantines, pomades, shampoos, cosmetic preparations, powders and the like. When used as (an) olfactory component(s) as little as 0.0001% of the compound(s), more preferably 1.0%, (based on weight of perfume composition) will suffice to impart a significant odor characteristic. Generally, no more than 7.0% of the compound(s) may be employed in such a manner to provide a method for modifying, enhancing or improving the organoleptic properties of perfumed compositions, colognes and perfumed articles by adding thereto an organoleptically effective amount of the novel chemicals of this invention.

The following examples are set forth herein to illustrate methods of synthesis of the compounds of this invention and their use in fragrance compositions. These examples are intended only to illustrate the preferred embodiments of this invention and are in no way meant to limit the scope thereof.

EXAMPLE 1

4-(1,1-dimethylethyl)-2-(1-methylethyl)-5-methylphenol

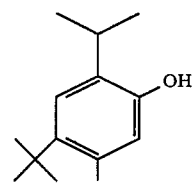

Thymol (360.0 g, 2.4 mol) was added to a cooled (0° C.) mixture of acetic acid (600 mL) and sulfuric acid (144 mL). The mixture was allowed to warm to 20°–25° C., after which, t-butanol (228 mL, 2.4 mol) was added dropwise over a one hour period. The mixture was stirred at 25° C. for one hour. An additional portion of t-butanol (114 mL, 1.2 mol) was then added dropwise over a one hour period. The mixture was stirred at 25° C. for 4 hours after which the mixture was poured into hexane (1 L) and water (1 L) and the layers separated. The aqueous layer was extracted with hexane (2×100 mL). The combined extracts were washed with water (3×200 mL), saturated sodium bicarbonate solution (2×100 mL), water (200 mL) and brine (2×100 mL). The solvents were evaporated and the residue distilled to provide 262 g (bp 135°–145° C., 6 mm) of material which was crystallized from hexane to give 215.2 g (43% yield, GLC purity 99.5%) of 4-(1,1-dimethylethyl)-2-(1-methylethyl)-5-methylphenol; mp 75.5°–76.5° C.; $^1$H-NMR (CDCl$_3$)δ 1.24 (6H, d, J=7 Hz), 1.38 (9H, s), 2.42 (3H, s), 2.95–3.42 (1H, m), 4.67 (1H, broad s), 6.48 (1H, s), 7.13 (1H, s); IR (CHCl$_3$)ν$_{max}$ 3575, 3340, 2940, 1605, 1670, 1490, 1450, 1400 cm$^{-1}$; MS m/e 206, 191, 149, 121; UVλ$_{max}$ (ethanol) 223 nm (ε=5650), 253 nm (ε=2260).

EXAMPLE 2

6-(1,1-dimethylethyl)-5-methyl-8-(1-methylethyl)-4H-1,3-benzodioxin

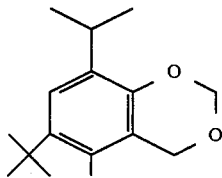

A solution of 4-(1,1-dimethylethyl)-2-(1-methylethyl)-5-phenol (51.5 g, 0.25 mol) in p-dioxane (125 mL) was added over a 30 minute period to a mixture of 40% formaldehyde solution (225 mL, 3.75 mol), p-dioxane (250 mL) and sulfuric acid (25 mL) heated at reflux. The mixture was cooled to 25° C. and the layers were separated. The aqueous layer was extracted with hexane (3×50 mL). The combined organic layers were diluted with hexane (250 mL) and washed with water (4×100 mL), saturated sodium bicarbonate solution (2×50 mL), water (200 mL), brine (200 mL) and dried (Na$_2$SO$_4$). Evaporation of solvents and distillation of the residue provided 25.9 g (42% yield, GLC purity 98%) of 6-(1,1-dimethylethyl)-5-methyl-8-(1-methylethyl)-4H-1,3-benzodioxin; bp 121°–124° C., 0.5 mm; $^1$H-NMR (CDCl$_3$)δ 1.20 (6H, d, J=7 Hz), 1.40 (9H, s), 2.18 (3H, s), 2.8–3.4 (1H, m), 4.72 (2H, s), 5.10 (2H, s), 7.03 (1H, s); IR (film) ν$_{max}$ 2950, 1585, 1470 cm$^{-1}$; MS m/e 248, 233, 218, 203, 175, 161; UVλ$_{max}$ (ethanol) 222 nm (ε=4450), 282 nm (ε=1450).

EXAMPLE 3

5-(1,1-dimethylethyl)-6-methyl-3-(1-methylethyl)-2-hydroxy benzenemethanol

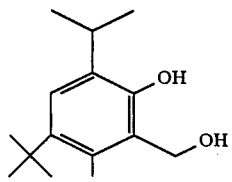

A mixture of 4-(1,1-dimethylethyl)-2-(1-methylethyl)-5-methylphenol (103.2 g, 0.5 mol), 40% formaldehyde solution (375 mL, 5 mol), potassium hydroxide (49.5 g, 0.75 mol) and poly(ethylene glycol) avg. M.W. 300 (1 g) was heated at reflux for 24 hour. The mixture was cooled to 25° C. and water (1 L) and hexane (700 mL) were added. The aqueous layer was extracted with hexane (2×100 mL). The combined organic extracts were washed with water (3×100 mL), brine (2×100 mL) and dried (Na$_2$SO$_4$). Evaporation of solvents and crystallization of the residue from hexane gave 10.2 g (8.6% yield) of 5-(1,1-dimethylethyl)-6-methyl-3-(1-methylethyl)-2-hydroxy benzenemethanol, mp 143°–146° C.; $^1$H-NMR (CDCl$_3$)δ 1.25 (6H, d, J=7 Hz), 1.40 (9H, s), 2.31 (3H, s), 3.0–3.6 (1H, m), 4.85 (2H, s), 7.01 (1H, s), 7.23 (1H, s); IR (CHCl$_3$)ν$_{max}$ 3550, 3350, 2940, 1575, 1470, 1360 cm$^{-1}$; M m/e 236, 218, 206, 203, 191, 161, UVλ$_{max}$ (ethanol) 224 nm (ε=6690), 287 nm (ε=2480).

EXAMPLE 4

2,5-dimethyl-6-(1,1-dimethylethyl)-8-(1-methylethyl)-4H-1,3-benzodioxin

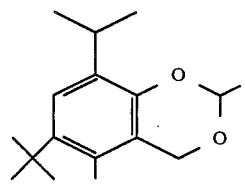

A mixture of 5-(1,1-dimethylethyl)-6-methyl-3-(1-methylethyl)-2-hydroxy-benzenemethanol (7.09 g, 0.03 mol), p-dioxane (150 mL), paraldehyde (13.2 g, 0.3 mol) and p-toluenesulfonic acid monohydrate (0.57 g, 0.003 mol) was heated at reflux for 1.5 hours. The mixture was cooled to 25° C., poured onto water (100 mL) and extracted with hexane (3×50 mL). The extracts were washed with saturated sodium bicarbonate solution (2×50 mL), water (4×50 mL), brine (50 mL) and dried (Na$_2$SO$_4$). Evaporation of solvents and distillation of the residue gave 5.56 g (71% yield, GLC purity 99%) of 2,5-dimethyl-6-(1,1-dimethylethyl)-8-(1-methylethyl)-4H-1,3-benzodioxin, bp 110°–120° C., 0.5 mm; $^1$H-NMR (CDCl$_3$)δ 1.20 (6H, d, J=7 Hz), 1.40 (9H, s), 1.54 (3H, d, J=5 Hz), 2.20 (3 H, s), 2.9–3.5 (1H, m), 4.80 (2H, s), 5.07 (1H, q, J=5 Hz), 7.10 (1H, s); IR (film)ν$_{max}$ 2940, 1585, 1410 cm$^{-1}$; MS m/e 262, 218, 203, 175, 161; UVλ$_{max}$ (ethanol) 225 (ε=6960), 281 (ε=2040).

EXAMPLE 5

6,8-(1,1-dimethylethyl)-4H-1,3-benzodioxin

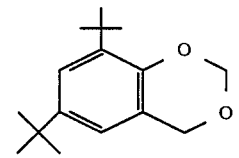

A solution of 2,4-(1,1-dimethylethyl)-phenol (103.1 g, 0.5 mol) in p-dioxane (350 mL) was added dropwise over a 50 minute period to a mixture of sulfuric acid (10 mL), water (20 mL), paraformaldehyde (150 g, 5 mol), and p-dioxane (500 mL). The mixture was heated at reflux for an additional 30 minutes after which, the mixture was cooled to 0° C. and a 20% potassium hydroxide solution (200 mL) and hexane (500 mL) were added. The aqueous layer was then extracted with hexane (2×100 mL). The organic extracts were washed with 20% potassium hydroxide solution (4×100 mL), water (3×100 mL), brine (100 mL) and dried (Na$_2$SO$_4$). Evaporation of solvents and distillation of the residue provided 99.75 g of material, bp 97°–135° C., 0.5 mm. Crystallization of the distilled product from methanol gave 81.0 g (65% yield, GLC purity 99%), 6,8-(1,1- dimethylethyl)-4H-1,3-benzodioxin, mp 52°–53° C.; $^1$H-NMR (CDCl$_3$)δ 1.32 (9H, s), 1.40 (9H, s), 4.93 (2H, s), 5.28(2H, s), 6.81(1H, s), 7.22(1H, s); IR(CHCl$_3$)ν$_{max}$ 2940, 1485, 1385, 1350 cm$^{-1}$; MS, m/e 248, 233, 218, 203, 175, 161; UVλ$_{max}$ (ethanol) 223 nm (ε=5400), 280 nm (ε=1700).

EXAMPLE 6

3,5-(1,1-dimethylethyl)-2-hydroxy-benzenemethanol

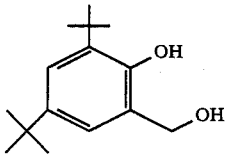

A mixture of 2,4-(1,1-dimethylethyl)-phenol (51.85 g, 0.25 mol), paraformaldehyde (37.5 g, 1.25 mol), dimethylformamide (500 mL) and KOH (11.8 g, 0.3 mol) was stirred at 35°–40° C. for 2 hours. Paraformaldehyde (7.5 g, 0.25 mol) was then added and the mixture was stirred at 40°–45° C. for 3 hours. The mixture was then heated at 60° C. for 1 hour. The mixture was cooled to 25° C., added to ice water and acidified with 40% sulfuric acid solution. The mixture was extracted with hexane (4×100 mL) and the extracts were washed with water (3×200 mL) and dried (Na$_2$SO$_4$). Evaporation of solvents and crystallization of the residue from hexane provided 19.3 g (33% yield) of 3,5-(1,1-dimethylethyl)-2-hydroxy-benzenemethanol, mp 100°–101° C.; $^1$H-NMR (CDCl$_3$)δ 1.30(9H, s), 1.45(9H, s), 2.18(1H, t, J=Hz), 4.82 (2H, d, J=5 Hz), 6.91 (1H, d, J=2 Hz), 7.32(1H, d, J=2 Hz), 7.57 (1H, s); IR(CDCl$_3$)ν$_{max}$ 3560, 3370, 2940, 1595, 1475, 1410; MS m/e 236, 218, 203, 161; UVλ$_{max}$ (ethanol) 226 nm (ε=4250), 282 nm (ε=2340).

EXAMPLE 7

6,8-(1,1-dimethylethyl)-2-methyl-4H-1,3-benzodioxin

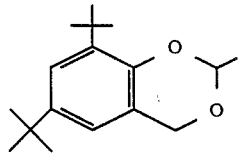

Reaction of 3,5-(1,1-dimethylethyl)-2-hydroxybenzenemethanol (7.03 g, 0.03 mol), paraldehyde (13.2, 0.3 mol), p-dioxane (150 mL) and p-toluenesulfonic acid hydrate (0.57 g, 0.003 mol) as described in Example 4, provided after distillation 4.12 g (52% yield, GLC purity 99%), of 6,8-(1,1-dimethylethyl)-2-methyl-4H-1,3-benzodioxin. Crystallization from methanol provided 3.0 g of pure benzodioxin, mp 59°–61° C.; $^1$H-NMR (CDCl$_3$)δ1.20 (9H, s), 1.30 (9H, s), 1.50 (3H, d, J=5 Hz), 4.83 (2H, dd, J=5 and 14 Hz), 5.10 (1H, q, J=6 Hz), 6.72 (1H, d, J=2 Hz), 7.10 (1H, d, J=2 Hz); IR (CDCl$_3$)λ$_{max}$ 2955, 1490, 1455, 1410 cm$^{-1}$; MS m/e 262, 218, 203, 177, 161; UVλ$_{max}$ (ethanol) 224 nm (ε=4650), 280 nm (ε=1190).

EXAMPLE 8

6,8-(1,1-dimethylethyl)-4H-1,3-benzodioxin

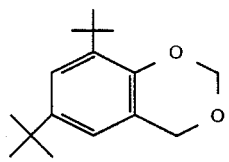

A mixture of 3,5-(1,1-dimethlethyl)-2-hydroxybenzenemethanol (2.36 g, 0.01 mol), paraformaldehyde (3.0 g, 0.1 mol), p-dioxane (50 mL) and 50% aqueous sulfuric acid solution (0.2 mL) was heated at reflux for 2 hours. The mixture was cooled (25° C.) and hexane (100 mL) and 40% potassium hydroxide solution (100 mL) were added. The mixture was stirred for 30 minutes and the aqueous layer was extracted with hexane (2×50 mL). The organic extracts were washed with 20% potassium hydroxide solution (2×50 mL), water (2×50 mL), brine (50 mL) and dried (Na$_2$SO$_4$). Kugelrohr distillation and chromatography provided 1.01 g (41% yield, GLC purity 95%) of 6,8-(1,1-dimethylethyl)-4H-1,3-benzodioxin.

EXAMPLE 9

6-(1,1-dimethylpropyl)-5-methyl-8-(1-methylethyl)-4H-1,3-benzodioxin

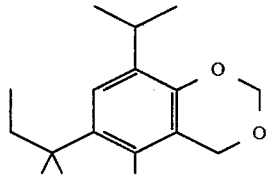

Reaction of 4-(1,1-dimethylpropyl)-2-(1-methylethyl)-5-methylphenol (22.02 g, 0.1 mol), which may be prepared as described by W. Koenigs and R. W. Carl, Chem. Ber., (1981) 25, 3892–3903, 40% formaldehyde solution (70 mL, 0.93 mol), p-dioxane (150 mL) and sulfuric acid (10 mL) according to the procedure described in Example 2, provided after chromatography and short-path distillation, 9.18 g (35% yield) of 6-(1,1-dimethylpropyl)-5-methyl-8-(1-methylethyl)-4H-1,3-benzodioxin (GLC purity 98%); $^1$H-NMR (CDCl$_3$)δ 0.70 (3H, t, J=7 HZ), 1.20 (6H, d, J=7 Hz), 1.35 (6H, s), 1.78 (2H, q, J=7 Hz), 2.15(3H, s), 3.0–3.5 (1H, m), 4.80 (2H, s), 5.17(2H, s), 7.03 (1H, s); IR (film) ν$_{max}$ 2950, 1575, 1470 cm$^{-1}$; MS m/e 262, 233, 217, 203, 175, 161; UVλ$_{max}$ (ethanol) 226 nm (ε=5530), 283 nm (ε=1520).

EXAMPLE 10

6,8-(1,1-dimethylethyl)-5-methyl-4H-1,3-benzodioxin

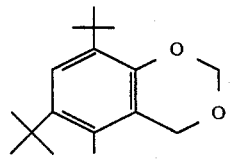

Reaction of 2,4-(1,1-dimethylethyl)-5-methylphenol (110 g, 0.5 mol) which may be prepared as described by W. Weinrich, *Ind. Eng. Chem.*, (1943) 35, 264–272, 40% formaldehyde solution (400 mL, 5.33 mol), p-dioxane (850 mL) and sulfuric acid (50 mL) according to the procedure described in Example 2, provided after distillation 40.2 g (31% yield, GLC purity 70%) of product having bp 120°–145° C., 0.5 mm. Crystallization from methanol provided 4.4 g (GLC purity 98%) of 6,8-(1,1-dimethylethyl)-5-methyl-4H-1,3-benzodioxin; mp 81.5°–82.5° C.; $^1$H-NMR (CDCl$_3$)δ1.37 (9H, s), 1.38 (9H, s), 2.17 (3H, s), 4.78 (2H, s), 5.15 (2H, s), 7.18 (1H, s); IR (CHCl$_3$)$\nu_{max}$ 2940, 1480, 1380, 1360 cm$^{-1}$; MS m/e 262, 232, 218, 189, 175; UVλ$_{max}$ (ethanol) 227 nm (ε=5110), 281 nm (ε=1700).

EXAMPLE 11

5,8-dimethyl-6-(1,1-dimethylethyl)-4H-1,3-benzodioxin

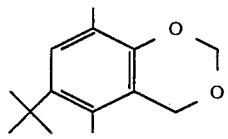

Reaction of 2,5-dimethyl-4-(1,1-dimethylethyl)-phenol (20.2 g, GLC purity 88%, 0.1 mol, which may be prepared as described by W. Weinrich, *Ind. Eng. Chem.* (1943) 35, 264–272), 40% formaldehyde solution (80 mL, 1.07 mol), p-dioxane (170 mL) and sulfuric acid (10 mL) according to the procedure described in Example 2, provided after distillation 13.05 g (59% yield, GLC purity 97%) of 5,8-dimethyl-6-(1,1-dimethylethyl)-4H-1,3-benzodioxin, bp 139° C., 3 mm; $^1$H-NMR (CDCl$_3$)δ 1.40 (9H, s), 2.21 (6H, s), 4.79 (2H, s), 5.14 (2H, s); 7.01 (1H, s); IR (film)$\nu_{max}$ 2940, 1580, 1475 cm$^{-1}$; MS m/e 220, 205, 190, 185, 147; UVλ$_{max}$ (ethanol) 225 nm (ε=4270), 281 nm (ε=1490).

EXAMPLE 12

A composition was prepared by mixing the following ingredients:

| Ingredients | Parts by Weight |
|---|---|
| Isobutyl salicylate | 10 |
| Butyl hydroxy anisole | 40 |
| Musk Ether (Compound 2 R$^1$ = CH$_3$) | 250 |
| Compound 4 (R$^1$, R$^2$ = H; R$^3$, R$^4$ = CH$_3$) | 700 |
| | 1000 |

The above composition possessed a strong musk odor resembling in character the commercially important nitro-musk 1.

EXAMPLE 13

Fougere for Men's Cologne

The composition was prepared by mixing the following ingredients:

| Ingredient | Parts by Weight |
|---|---|
| Methyl naphthyl ketone | 10 |
| Methyl anthranilate | 5 |
| Indole 10% | 5 |
| α-amylcinnamaldehyde | 5 |
| terpineol | 10 |
| Oil Vetiver Haiti | 10 |
| Oil Sandalwood | 20 |
| Oil Patchouli | 10 |
| Benzyl acetate | 40 |
| Rhodinol | 60 |
| Oil Geranium Reunion | 10 |
| Phenylethyl alcohol | 15 |
| Phenylacetaldehyde 10% | 10 |
| Anisic aldehyde | 50 |
| Heliotropin | 25 |
| Ethylvanillin | 5 |
| Coumarin | 15 |
| Isoeugenol | 5 |
| Hydroxycitronellal | 75 |
| Oil Basil | 10 |
| Oakmoss absolute | 10 |
| Labdanum absolute 10% | 10 |
| Oil Orange Florida | 20 |
| Oil Petitgrain Paraquay | 10 |
| Oil Lavender 40/42% | 40 |
| Oil Mandarin | 10 |
| Oil Lemon California, dist. | 25 |
| Benzyl salicylate | 50 |
| Isoamyl salicylate | 100 |
| Composition from Example 12 | 125 |
| Ionone Alpha | 5 |
| Oil Bergamont rectified | 200 |
| | 1000 |

The inclusion of the novel compound 4 (R$^1$, R$^2$=H, R$^3$, R$^4$=CH$_3$) imparts to the fragrance composition a musk note which is reminiscent of the effect produced by nitro-musk 1. In addition, the other components of the fragrance are enhanced.

EXAMPLE 14

Shampoo

A shampoo may be made according to the following formula:

| Ingredients | Parts by Weight |
|---|---|
| Water | 810 |
| Calcium alginate | 20 |
| Sodium citrate | 10 |
| Triethanolamine lauryl sulfate | 10 |
| Glycerol | 50 |
| Methyl p-hydroxybenzoate | 1 |
| Organoleptic agent | 9 |
| | 1000 |

Use of a compound of the invention or a composition such as Example 12 as the organoleptic agent may impart a musk-like odor to the shampoo.

EXAMPLE 15

Cleansing Cream

A cleansing cream may be prepared according to the following formula:

| Ingredients | Parts by Weight |
|---|---|
| Mineral oil | 300 |
| Lanolin, anhydrous | 30 |
| Stearic acid | 120 |
| Carbitol | 50 |
| Triethanolamine | 15 |
| Water | 480 |
| Organoleptic agent | 5 |
| | 1000 |

Use of a compound of the invention or a composition such as Example 12 as the organoleptic agent may impart a musk-like odor to the cleansing cream.

EXAMPLE 16

Baby Powder

A scented baby powder may be prepared according to the following formula:

| Ingredients | Parts by Weight |
| --- | --- |
| Talc | 900 |
| Lithium stearate | 25 |
| Kaolin | 50 |
| Organoleptic agent | 25 |
| | 1000 |

Use of a compound of the invention or a composition such as Example 12 as the organoleptic agent may impart a musk-like odor to the baby powder.

We claim:

1. The compounds having the structure

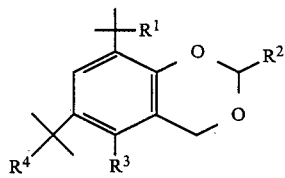

wherein $R^1$ to $R^4$ are hydrogen or lower alkyl ($C_1$ to $C_5$).

2. The compounds according to claim 1 wherein the compound contains no more than 18 carbon atoms.

3. The compounds according to claim 1 wherein $R^1$ and $R^2$ are hydrogen or methyl and $R^3$ and $R^4$ are hydrogen or lower alkyl ($C_1$ to $C_5$).

4. The compound according to claim 1 wherein $R^1$ and $R^2$ are hydrogen and $R^3$ and $R^4$ are methyl.

5. The compound according to claim 1 wherein $R^2$ and $R^3$ hydrogen and $R^1$ and $R^4$ are methyl.

6. The compound according to claim 1 wherein $R^2$ is hydrogen and $R^1$, $R^2$ and $R^3$ are methyl.

7. The compound having the structure

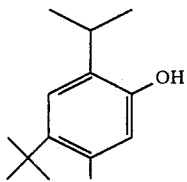

8. A fragrance composition comprising an organoleptically effective amount of a compound of claim 1 and at least one other organoleptic agent.

9. A fragrance composition comprising an organoleptically effective amount of a compound of claim 2 and at least one other organoleptic agent.

10. A fragrance composition comprising an organoleptically effective amount of a compound of claim 3 and at least one other organoleptic agent.

11. A fragrance composition comprising an organoleptically effective amount of a compound of claim 4 and at least one other organoleptic agent.

12. A fragrance composition comprising an organoleptically effective amount of a compound of claim 5 and at least one other organoleptic agent.

13. A fragrance composition comprising an organoleptically effective amount of a component of claim 6 and at least one other organoleptic agent.

14. A fragrance composition which comprises an amount of the compound of any of claims 1 to 6 wherein said effective fragrance imparting amount is an amount from about 0.0001% to about 80% by weight of said fragrance component.

15. A fragrance composition which comprises an amount of the compound of any of claims 1 to 6 wherein said effective fragrance imparting amount is an amount from about 0.0001% to 7.0% by weight of said perfumed article.

16. A method for imparting a musk fragrance to a consumable material selected from the group consisting of perfume compositions, colognes and perfumed articles comprising the step of adding to said consumable material an effective amount of the compound of any of the claims 1 to 6.

17. A method for altering, modifying or enhancing the organoleptic properties of perfume compositions, colognes and perfumed articles which comprises adding thereto an organoleptically effective amuont of the compound of any of claims 1 to 6.

18. A compound having the name: '5,8-dimethyl-6-(1,1-dimethylethyl)-4H-1,3-benzodioxin.

* * * * *